United States Patent
Brokish et al.

(10) Patent No.: US 9,524,567 B1
(45) Date of Patent: Dec. 20, 2016

(54) METHOD AND SYSTEM FOR ITERATIVE COMPUTED TOMOGRAPHY RECONSTRUCTION

(71) Applicant: InstaRecon, Urbana, IL (US)

(72) Inventors: Jeffrey Brokish, Savoy, IL (US); Yoram Bresler, Urbana, IL (US); Luke Pfister, Urbana, IL (US)

(73) Assignee: InstaRecon, Urbana, IL (US)

( * ) Notice: Subject to any disclaimer, the term of this patent is extended or adjusted under 35 U.S.C. 154(b) by 0 days.

(21) Appl. No.: 14/746,434

(22) Filed: Jun. 22, 2015

Related U.S. Application Data (60) Provisional application No. 62/015,446, filed on Jun. 22, 2014.

(51) Int. Cl.
| | | |
|---|---|---|
| G06K 9/00 | (2006.01) | |
| G06T 11/00 | (2006.01) | |
| A61B 6/03 | (2006.01) | |
| A61B 6/00 | (2006.01) | |
| G06T 7/00 | (2006.01) | |

(52) U.S. Cl.
CPC ............ *G06T 11/006* (2013.01); *A61B 6/032* (2013.01); *A61B 6/5205* (2013.01); *G06T 7/0012* (2013.01); *G06T 7/0032* (2013.01); *G06T 2207/10081* (2013.01); *G06T 2207/10116* (2013.01); *G06T 2207/30004* (2013.01); *G06T 2211/424* (2013.01); *G06T 2215/16* (2013.01)

(58) Field of Classification Search
None
See application file for complete search history.

(56) References Cited

U.S. PATENT DOCUMENTS

| | | | | |
|---|---|---|---|---|
| 6,005,916 A | * | 12/1999 | Johnson | A61B 5/05 378/87 |
| 8,971,599 B2 | * | 3/2015 | DeMan | G06T 11/006 378/4 |
| 2011/0142316 A1 | * | 6/2011 | Wang | G06T 11/006 382/131 |
| 2012/0155728 A1 | * | 6/2012 | DeMan | G06T 11/006 382/131 |
| 2013/0343672 A1 | * | 12/2013 | Yu | G06T 11/003 382/276 |

(Continued)

OTHER PUBLICATIONS

Combettes, P.L., et al., "Signal recovery by proximal forward-backward splitting", Multiscale Model. Simul., vol. 4, Issue 4, (2005), pp. 1168-1200.

(Continued)

*Primary Examiner* — Avinash Yentrapati
(74) *Attorney, Agent, or Firm* — Greer, Burns & Crain, Ltd.; Steven P. Fallon (57) ABSTRACT

Methods and systems for iterative computed tomography add an auxiliary variable to the reconstruction process, while retaining all variables in the original formulation, A weighting operator or filter can be applied that causes the Hessian with respect to an image of the cost function to be well-conditioned. An auxiliary sinogram variable distinct from both a set of actual image measurements and from the set of projections computed based on an image can be applied to iteratively update during the statistical iterative image reconstruction, with applied conditions that causes the Hessian with respect to an image of the cost function to be well-conditioned.

26 Claims, 3 Drawing Sheets

(56) References Cited

U.S. PATENT DOCUMENTS

| | | | | |
|---|---|---|---|---|
| 2014/0140599 A1* | 5/2014 | Kim | ..................... | G06T 11/006 382/131 |
| 2014/0369580 A1* | 12/2014 | Yu | ......................... | G06T 11/006 382/131 |
| 2014/0369581 A1* | 12/2014 | Fu | ......................... | G06T 11/006 382/131 |
| 2015/0287223 A1* | 10/2015 | Bresler | ................ | G06T 11/006 382/131 |

OTHER PUBLICATIONS

Eckstein, J., "Augmented Lagrangian and Alternating Direction Methods for Convex Optimization: A Tutorial and Some Illustrative Computational Results", RUTCOR Research Report RRR 32-2012, (Dec. 2012), 35 pages.

Figueiredo, M.T., et al., "Gradient projection for sparse reconstruction: Application to compressed sensing and other inverse problems", IEEE Journal of Selected Topics in Signal Processing, vol. 1, No. 4, (Dec. 2007), pp. 586-597.

\* cited by examiner

METHOD AND SYSTEM FOR ITERATIVE COMPUTED TOMOGRAPHY RECONSTRUCTION

PRIORITY CLAIM AND REFERENCE TO RELATED APPLICATION

The application claims priority under 35 U.S.C. §119 from prior provisional application Ser. No. 62/015,446, which was filed Jun. 22, 2014.

STATEMENT OF GOVERNMENT INTEREST

This invention was made with government support under R44EB014669 awarded by National Institutes of Health, National Center for Advancing Translational Sciences (NCATS) and National Institute of Biomedical Imaging and Bioengineering (NIBIB). The government has certain rights in the invention.

FIELD

A field of the invention is computed tomography. The invention is applicable to various computed tomography techniques, including, for example, X-ray Computed Tomography (CT), single photon emission computed tomography (SPECT), and positron emission tomography (PET)

BACKGROUND

Computed tomography techniques including X-ray Computed Tomography (CT), single photon emission computed tomography (SPECT), positron emission tomography (PET) are well-established imaging modalities. Conventional image reconstruction in such imaging modalities and others has been performed using a method known as filtered backprojection (MP). More recently, iterative image reconstruction methods have been introduced, with the main motivation being x-ray dose reduction. One goal of the iterative techniques is to lower the dose of radiation experience by a subject being imaged. The lower doses and under sampling (when used, e.g., to reduce dose) provide challenges to compute high contrast and clear images. Another goal of iterative techniques, is to provide high-quality reconstruction from data acquired by advanced detector systems such as photon counting detectors, for which FBP may not provide the desired quality. Recent iterative techniques utilized an image fidelity function to encourage fidelity to the measured data, and an edge-preserving regularization function such as total variation or qGGIVERF that encourages smoothness in image areas with little variation, while recovering sharp boundaries to preserver image resolution.

DeMan et al. U.S. Pat. No. 8,971,599 discloses methods for iterative tomographic reconstruction, Three embodiments are discussed that use a ramp filter as a preconditioner. in a first embodiment, the iteration applies a deconvolution filter and reevaluates to see if completion criteria have been satisfied. This first embodiment uses a change of variables (that is, replacing all instances of the image variable x with another variable z, using the equivalence x=Fz for a filter F). The approach of the first embodiment is highly similar to the classical formulation. of preconditioning. In a second embodiment, a preconditioner is applied to the simultaneous image update steps of an iterative reconstruction, where the preconditioner approximates the inverse Hessian of the cost function being optimized. In a variation, the preconditioner is applied only to the data, fidelity term (called data fit term in the '599 patent) and not to the regularization term. This strategy is intended to accommodate edge preserving priors, which are commonly used in current iterative reconstruction methods. However, by applying the preconditioner in this way, it ceases to be a proper preconditioner. Instead, this approach fundamentally alters the minimization process such that the fixed point of the iteration no longer corresponds to the fixed point of the original update sequence. One drawback of the techniques in the '599 patent arises in the common case that statistical weighting matrices are used in the update steps. These weighting matrices degrade the approximation of the ramp filter (preconditioner) as an inverse Hessian operation, and therefore degrade the preconditioning effect. In particular, the presence of the weighting matrix W, which often has large dynamic range and therefore causes the Hesssian of the data fidelity term in the cost function to be poorly conditioned, has a detrimental effect on the rate of convergence of the iterative algorithm, ultimately requiring more iterations to achieve a desired accuracy.

SUMMARY OF THE INVENTION

Embodiments of the invention include methods and systems for iterative computed tomography. In preferred methods and systems of the invention, an auxiliary variable is added to the reconstruction process, while retaining all variables in the original formulation. Preferred embodiments apply a weighting operator or filter that causes the Hessian with respect to image of the cost function to be well-conditioned. In preferred embodiments, an auxiliary sinogram variable distinct from both a set of actual image measurements and from a set of projections computed based on the image is applied to iteratively update during the statistical iterative image reconstruction, with applied conditions that causes the Hessian with respect to image of the cost function to be well-conditioned:

DETAILED DESCRIPTION OF THE PREFERRED EMBODIMENTS

Unlike the techniques in the '599 patent discussed in the background, preferred methods of the invention do not degrade the approximation of the ramp filter as an inverse Hessian operation. Preferred methods instead relate the image to an auxiliary variable without statistical weighting, but using a ramp filter (or other norm weighting), while the statistical weighting can remain in a different term, relating the measured projection data derived from the CT scan data to the auxiliary variable, without using the ramp filter. More generally, preferred embodiments apply a weighting operator or filter that causes the Hessian with respect to image of the cost function to be well-conditioned. The auxiliary variable is added to the reconstruction process, while retaining all variables in the original formulation. The preferred iterative reconstruction methods use both the image variable and the auxiliary variable, and specifically updates to the image variable depend on the auxiliary variable, but not on the measured projection data, and the updates to the image variable do not need to include the statistical weighting. Also unlike the variations of the '599 patent that alter the minimization process such that the fixed point of the iteration no longer corresponds to the fixed point of the original update sequence, methods of the invention maintain mathematical equivalence with the solution of the original update process.

Preferred methods and systems provide for iterative reconstruction tomography images including, for example, CT images, SPECT and PET images. Preferred embodiments can reduce the computation needed to produce an image of desired quality using an iterative algorithm. This can be used to obtain results more quickly using the same computing hardware, or to reduce the cost and/or the size and weight and/or the power consumption of the computing hardware needed to produce the results in a desired time. Because iterative reconstruction can be used to reduce the x-ray dose to which the subject is exposed during a CT scan, and/or improve image quality and reduce artifacts, e.g., due to metal implants, the preferred methods and systems can be used to provide the same benefits at a lower cost and/or at a higher patient throughput and smaller delay for reconstruction compared to traditional CT methods and systems.

Those knowledgeable in the art will appreciate that embodiments of the present invention lend themselves well to practice in the form of computer program products. Accordingly, it will be appreciated that embodiments of the present invention may comprise computer program products comprising computer executable instructions stored on a non-transitory computer readable medium that, when executed, cause a computer to undertake methods according to the present invention, or a computer configured to carry out such methods. The executable instructions may comprise computer program language instructions that have been compiled into a machine-readable format. The non-transitory computer-readable medium may comprise, by way of example, a magnetic, optical, signal-based, and/or circuitry medium useful for storing data. The instructions may be downloaded entirely or in part from a networked computer. Also, it will be appreciated that the term "computer" as used herein is intended to broadly refer to any machine capable of reading and executing recorded instructions, it will also be understood that results of methods of the present invention may be displayed on one or more monitors or displays (e.g., as text, graphics, charts, code, etc.), printed on suitable media, stored in appropriate memory or storage, etc.

Figure 1:
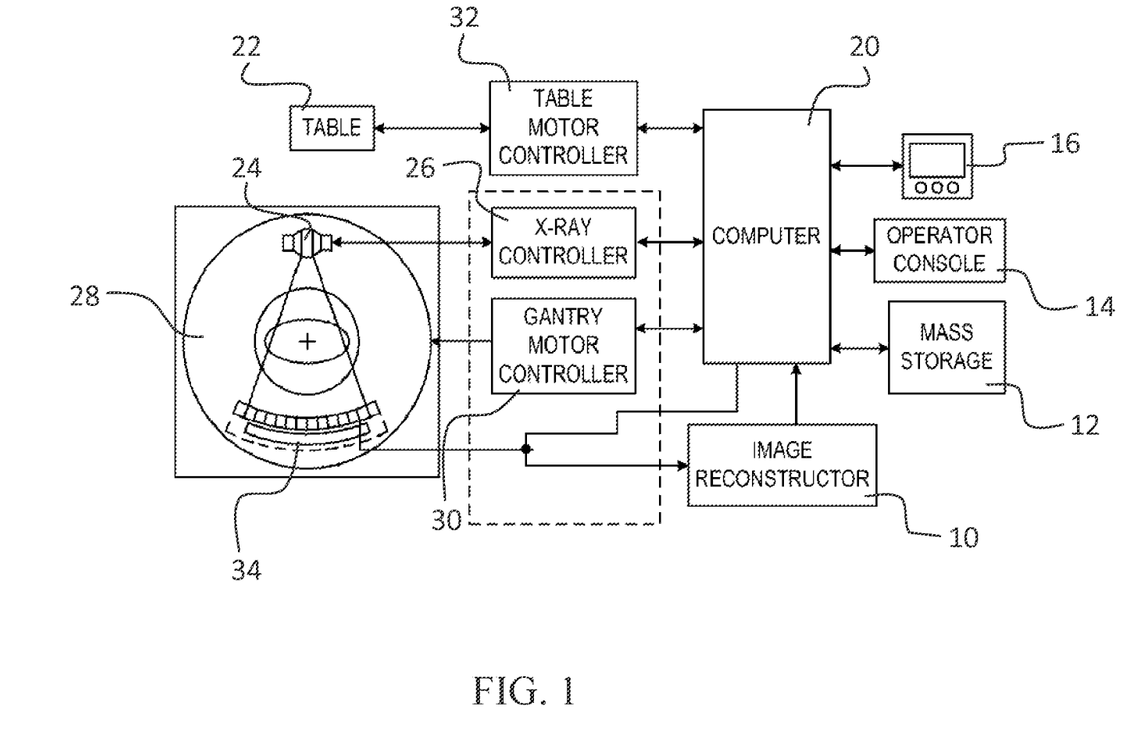
FIG. 1 is a schematic diagram of a preferred embodiment iterative computed tomography system of the invention.

Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale FIG. 1 illustrates a system of the invention that includes an image reconstructor 10 that conducts iterative reconstruction with an auxiliary variable and applies a weighting operator or filter that causes the Hessian with respect to image of the cost function to be well-conditioned, such as by adding ramp filtering to the reconstruction process. Image data is stored in mass storage 12. An operator console 14 is used to direct system operations, and a display 16 can display reconstructed images. A computer 20 coordinates system operations and data acquisition. During operation of the system, projection data of a subject under examination lying on an imaging table 22 (schematically represented but being movable within the center of a gantry 28) is acquired by operating an X-ray source 24 under control of an X-ray controller 26 while spinning the gantry 28 under control of a gantry motor controller 30, and moving the table 22 under control of a table motor controller 32, with the controllers being coordinated by the computer 20, instructed by commands given by an operator through the operator console 14. A detector 34 detects radiation passing through the subject. Detected electrical signals at the detector are digitized and transmitted to the image reconstructor 10 and computer 20, which stores reconstructed images in mass storage 12. After preprocessing and correction, projection data are derived from the detector data and fed to an iterative reconstruction module of the image reconstructor 10. The image reconstructor 10 can be a software module implementing the method of this invention and running on the computer, or a separate physical device, itself a computer running the software implementing a preferred method of the invention. Alternatively, the image reconstructor can be implemented in a combination of hardware, firmware, and software, including GPUs (graphical processing units), FPGAs, ASICS, circuit boards, and various electronic or electro-optical components.

A preferred iterative reconstruction module applies an iterative reconstruction with an auxiliary variable and a weighting operator or filter that causes the Hessian with respect to image of the cost function to be well-conditioned. In preferred embodiments, the weighting operator or filter is a ramp filter. Generally, the reconstruction method of preferred embodiments is related to iterative reconstruction techniques that use the Augmented Lagrangian. Augmented Lagrangian methods of iterative reconstruction (IR) converge more quickly than techniques that directly minimize the objective function used in the iterative reconstruction, in particular in the case of weighted or complicated discrepancy terms between the acquired sinogram and the sinogram computed based on the image.

Before discussing introductory concepts and the preferred the iterative reconstruction, symbols used in the following description and the in claims will be defined. The following table defines symbols that are used.

| Symbol | Definition |
| --- | --- |
| f | Image variable - Representing a 2D array of values defining pixels in the case of 2D imaging, or a 3D array of values defining voxels in the case of 3D imaging |
| g | A measured sinogram variable that is a set of actual measurements derived from a set of actual CT data. It is a 2D array of values in the case of 2D imaging, and can be either a 2D or a 3D array of values in the case of 3D imaging |
| R | Projection operator ("Projector"), also known as the "system matrix" |
| Rf | Set of measurements computed based on the image |
| h(Rf, g) | A measure of the discrepancy between the acquired measurement data g and the computed measurements Rf |
| Φ(f) | Regularization functional that represents prior information about the image f. |
| W | Singoram discrepancy weighting matrix or operator |
| u | Auxiliary sinogram variable representing an approximation to the set of measurements computed based on the image. This variable has the same dimensions as the measured sinogram variable g. |
| η | Auxiliary sinogram variable, serving as a Lagrange multiplier (also known as dual variable) |
| $R^T$ | Adjoint of the Projection operator, also known as backprojection operator |
| $f^n$, $u^n$, $\eta^n$, etc. | The values of f, u, η, etc. at iteration number n |
| L(u, f, η) | Augmented Lagrangian (AL) (with completion of the square) |
| $L_\rho$(u, f, η) | ρ - weighted Augmented Lagrangian (ρ - weighted AL) (with completion of the square) |
| $\nabla_f^2$ L(u, f, η) | The Hessian of the AL with respect to f |
| $R^T \Gamma R$ | The Hessian with respect to f of the image discrepancy term of the AL |
| s | Auxiliary sinogram variable representing an approximation to the auxiliary sinogram variable u, or (in the case of ADMM-ρ with extended weighting and additional splitting) chosen such that its rebinned version Es represents an approximation to the auxiliary sinogram variable u |
| $\eta_u$, $\eta_s$, $\eta_1$, $\eta_2$ | Auxiliary sinogram variables, serving as Lagrange multipliers (also known as dual variables) |
| z | Auxiliary image domain variable approximating the image |
| Γ | Weighting operator |
| $E^T \rho E$ | Weighted ramp filtering operation |
| $\rho^{1/2}$ | Square root of the ρ operator (e.g., square root of the ramp filter). |
| $\hat{\rho}$ | The image domain representation or approximate representation of the ρ operator. |
| $\hat{\rho}^{\frac{1}{2}}$ | Square root of the image domain representation or approximate representation of the ρ operator. |
| x | Image-domain auxiliary variable defined such that $\hat{\rho}^{\frac{1}{2}} x$ is the image, or approximates the image. "pre-image auxiliary variable". |

Denote the reconstructed image by the image variable f. Image variable f can represent a 2D array of numbers in the case of 2D imaging, e.g., cross-sectional CT, or a 3D array of numbers in the case of 3D imaging, e.g., conebeam or helical conebeam CT. As known to artisans, such arrays may be organized in various desired forms in computer memory. Because any data array of any dimension can be arranged into a 1D array, or vector, for the purposes of this disclosure, it will be convenient to consider all data arrays, regardless of dimension, as vectors. It will also be noted, as used in the disclosure and the claims, that a vector approximately proportional to the gradient indicates that the vector is not perpendicular to the gradient (not equal to π/2, and preferably less than π/2).

A typical formulation for conventional iterative reconstruction involves minimization of a cost function to generate the reconstructed image f. This minimization problem and cost function can be generally written as $$f_{opt} = \underset{f}{\arg\min}\, h(Rf, g) + \Phi(f) \qquad (1)$$

where $f_{opt}$ is the final reconstructed image. The measured sinogram variable g usually corresponds to a 2D or 3D data array. For example, it would correspond to a 2D data array in the case of 2D imaging, or in the case of 3D helical imaging with a line detector when g is indexed by view angle and detector index. It would correspond to a 3D array, for example in the case of 3D conebeam CT imaging with a multirow or area detector. In some applications, such as dual or multi-energy (also called multispectral) 3D CT, the measured sinogram variable g may correspond to a 4 dimensional array. Again, for the purposes of this disclosure, we will consider g to be a vector.

The measured sinogram variable g is generated from CT data by conventional techniques, such as those described by J. Hsieh, "Computed Tomography: Principles, Design, Artifacts, and Recent Advances, Second Edition, SPIE, Wash. USA, 2009, which may include negative logarithm, and various corrections steps for deviations from ideal models. In the case of iterative reconstruction, fewer corrections may be used in generating the measured sinogram data g, and instead some of the non-idealities and even the negative logarithm operation may be included, if desired, in the modeling incorporated into the iterative reconstruction, as described below. The projection operator R ("Projector"), also known as the system matrix, incorporates the model of the data acquisition process. For example, it might account for the line integral measurement, for the shape of the X-ray beam and of the focal spot, for the shape of the voxel or other basis function used to represent the image, for the geometry of the CT scanner, for the shape and properties of the detector, etc. Given an image f, the quantity Rf is the set of measurements (also called "sinogram" or "projections") computed based on the image f. The function h(Rf,g) is a measure of the discrepancy between the acquired projection data g and the computed projection data Rf generated by the current image estimate off using the projection operator R. Accordingly, the first term in the cost function in (1) is sometimes called a data fidelity term. The adjoint $R^T$ of R is a backprojector operator. This backprojection operator may however, be somewhat different from conventional approximate backprojection operators used in filtered back projection algorithms, which may not have an exact adjoint relationship to a desired projector R.

Examples of h include a negative log-likelihood term, such as a Poisson-likelihood, a weighted sum-of-squared deviations, or other nondecreasing and typically convex functional, such as a weighted sum of generalized Huber functions of elements of the difference g–Rf. With such or other choices of h, it too can be used to express physical and/or statistical modeling aspects of the CT data acquisition, which may result in g not exactly corresponding to true projections or sinogram, as described by J. Hsieh, "Computed Tomography: Principles, Design, Artifacts, and Recent Advances, Second Edition, SPIE, Wash. USA, 2009.

The step of generating g from the CT data may be even reduced, if desired, to no operations (i.e., using the actual CT data in unmodified form), by appropriate choice of function h (e.g, incorporating desired transformations or corrections into h), although it is usually computationally advantageous to perform at least some of these transformations and corrections in a separate step of generating g.

The $\Phi(f)$ term in (1) is a regularization functional that represents prior information about the image f. Common choices for $\Phi(f)$ encourage smoothness in the image by penalizing local differences, that is, differences between voxels in a small neighborhood about each voxel. Typically non-quadratic penalties, with notable examples including generalized Huber functions of the local differences, the so-called qGGMRF (random field) penalty, total variation, or other penalties that promote sparsity of the local differences or of some transform of the image, are used to introduce an edge preserving property to the regularization, or capture additional properties of the images of interest.

The iterative reconstruction algorithm involves updates to the algorithm variables to progressively perform the minimization in (1). A stopping criterion is employed to terminate the iterative algorithm. The stopping criterion might include, for example, running for a fixed number of iterations, examining the discrepancy (e.g., some norm of the difference g−Rf) between the measured sinogram g and computed measurements (projections) Rf, or detecting when the maximum absolute value of an element (pixel or voxel, as the case may be) of an update of the image f is below some threshold.

As a specific example, we consider the penalized weighted least squares (PWLS) formulation for h, although the method described here is generally applicable to other functions. The PWLS cost function and associated optimization problem are $$f_{opt} = \operatorname{argmin}_{f} \frac{1}{2} \|g - Rf\|_W^2 + \Phi(f) \qquad (2)$$

The weighted squared norm $\|v\|_\Gamma^2$ of a vector v denotes the quantity $v^T\Gamma v$, for a positive-definite symmetric operator or matrix $\Gamma$, where $v^T$ denotes the transpose of vector v, or equivalently $\|v\|_\Gamma^2 = \langle \Gamma v, v \rangle$, where $\langle \cdot, \cdot \rangle$ denotes the Euclidean inner product between vectors, and $\Gamma v$ is the application of the linear operator $\Gamma$ to v. (Alternatively, the square of the weighted norm can be implemented as $\|\Gamma^{1/2}v\|_2^2 = \langle \Gamma^{1/2}v, \Gamma^{1/2}v \rangle$, where $\Gamma^{1/2}$ is a square root of operator $\Gamma$, and satisfies $(\Gamma^{1/2})^T \Gamma^{1/2} = \Gamma$, where $A^T$ denotes the adjoint of operator A.) The notation for the norm simplifies to $\|v\|_2$ when the weight operator is the identity operator. Here too, as in the rest of this disclosure, vector v may represent a physical multidimensional array. In Equation (2) W is a diagonal matrix that encapsulates the statistical or other modeling information about the data g. For example, the elements on the diagonal of W can be set to the inverse of an estimate of the variance of each measurement $g_i$, as follows $$W_{ii} = I_0 e^{-g_i} \qquad (3)$$

where $I_0$ denotes the number of incident photons when measured in an air scan, with or without a bow-tie filter as appropriate. Alternatively, W can be set to some other weighting that represents the confidence about particular measurements. Another typical usage is to down-weight rays passing through highly attenuating objects such as metal.

Direct minimization of the cost function in (1) can be challenging, due to the large scale of the problem along with the presence of the weighting matrix W, which often has large dynamic range and therefore causes the Hesssian of the data fidelity term in the cost function to be poorly conditioned, or other aspects of h(Rf−g), which make evaluation of it or of its gradients computationally demanding, and/or require many iterations to approach convergence. A variable splitting technique addresses these issues. The variable splitting technique converts the unconstrained minimization of (1) to the constrained minimization problem:

$$f_{opt} = \operatorname{argmin}_{f} h(u, g) + \Phi(f) \qquad (4)$$

such that u=Rf

This is in turn converted back to an unconstrained minimization problem using the Augmented Lagrangian (AL) (with completion of the square)

$$L(f, u, \eta) = h(u, g) + \Phi(f) + \frac{\mu}{2}\|u - Rf - \eta\|_2^2 \qquad (5)$$

Here u is an auxiliary sinogram-domain variable, representing an approximation to the measurements Rf computed based on the image. Variable $\eta$ is another auxiliary sinogram variable, serving as a Lagrange multiplier (also known as dual variable). We refer to the first term in Equation (5) as the sinogram discrepancy term, and to the third term as the image discrepancy term. Significantly, the constant $\mu$ only affects the rate of convergence of the algorithm, not the final resulting image at the point of complete convergence.

The AL can be used in the Augmented Lagrangian Method (ALM), which involves the iteration $$(u^{n+1}, f^{n+1}) = \operatorname*{argmin}_{u,f} L(u, f, \eta^n) \qquad (6)$$

$$\eta^{n+1} = \eta^n - (u^{n+1} - Rf^{n+1}) \qquad (7)$$

which is repeated for increasing values of n starting from some appropriate initial values at n=0, until some convergence criterion is met. Here symbols with superscript n denote the values of the corresponding variable in iteration number n. Typical choices for initial values for the variables are to set $f^0$ as the FBP reconstruction of sinogram data g, set $u^0 = Rf^0$, and set $\eta^0 = 0$.

Variations on the ALM include algorithms that perform the minimization in (6) approximately by block coordinate descent, alternating between minimization with respect to f and u, with the other variable held fixed [J. Eckstein, "Augmented Lagrangian and Alternating Direction Methods for Convex Optimization; A Tutorial and Some Illustrative Computational Results," RUTCOR Research Report RRR 32-2012, December 2012]. Typically, the most challenging minimization is the one with respect to f, because of the presence of R.

Auxiliary Variable Preferred Method

The present inventors have recognized that the image discrepancy term, i.e., the norm term in (5) can be replaced by a weighted two-norm $\|\cdot\|_\Gamma^2$ or even semi-norm with a positive non-negative definite operator $\Gamma$, which can provide advantages in implementation or in convergence rate. Depending on the choice of weighting operator $\Gamma$, existing theoretical convergence analyses for the resulting optimization algorithms may not exactly apply, but empirical results can still be favorable. In preferred embodiments, particular choices of weighting operators provide advantages. Advantageous choices for $\Gamma$ are those for which the Hessian $\nabla_f^2 L(u, f, \eta) = R^T \Gamma R + \nabla_f^2 \Phi(f)$ of the AL with respect to f (which is well-defined when $\Phi$ is twice differentiable) or the Hessian $R^T \Gamma R$ with respect to f of the image discrepancy term (last term) of the AL, are well-conditioned (e.g., approximately equal or approximately proportional to the identity operator). This will speed up convergence of the minimization with respect to f, and therefore reduce the computation for the entire iterative algorithm.

Example advantageous choices of $\Gamma$ that improve the conditioning of the composite operator $R^T \Gamma R$ are described next. Consider data in the projection domain denoted by q(t, θ) for 2D (cross-sectional) imaging, or by q(t, θ, r) for 3D imaging, where t denotes the detector index along a detector row, θ denotes view (or x-ray source) angle, and r denotes detector row index. Then, one favorable choice for the operator $\Gamma$ is the ρ operator, which performs a 1-D filtration (in the t variable) along each row in the projection domain. The frequency response of the ρ operator is the so-called ramp filter response |ω| for frequency variable ω. Owing to the length of the impulse response of this filter in the spatial domain, the ρ operator is typically applied in the frequency domain, using the FFT (Fast Fourier Transform), as is done with conventional filtered backprojection reconstruction. An alternative realization of the ρ operator is to use lower order IIR (Infinite Impulse Response) or FIR (Finite Impulse Response) filters applied in the projection domain that approximate the |ω| response at lower computational cost.

This choice $\Gamma = \rho$ of weight operator in the AL produces the ρ-weighted AL $L_\rho$, given in the following Equation (8)

$$L_\rho(f, u, \eta) = h(u, g) + \Phi(f) + \frac{\mu}{2}\|u - Rf - \eta\|_\rho^2 \quad (8)$$

This leads to the Hessian of the image discrepancy term (the third term) in the ρ-weighted AL (8) being equal to $R^T \rho R$, which is the identity operation for parallel beam geometries in the continuous variable formulation, or an approximation of the identity operation in the discrete and divergent beam (e.g. fan and cone, with circular or helical) geometries. Thus, minimization of (8) with respect to f is approximately preconditioned by this construction.

Artisans will appreciate that the auxiliary sinogram variable u is distinc from both the measured sinogram g, and from the measurements computed based on the image, Rf.

The utility in this choice of weight can be demonstrated, with the specific example of the PWLS (Penalized Weighted Least Squares) choice for h, and a particular AL-based scheme, although the technique is applicable to other cost function formulations, and other AL-based schemes.

Figure 2:
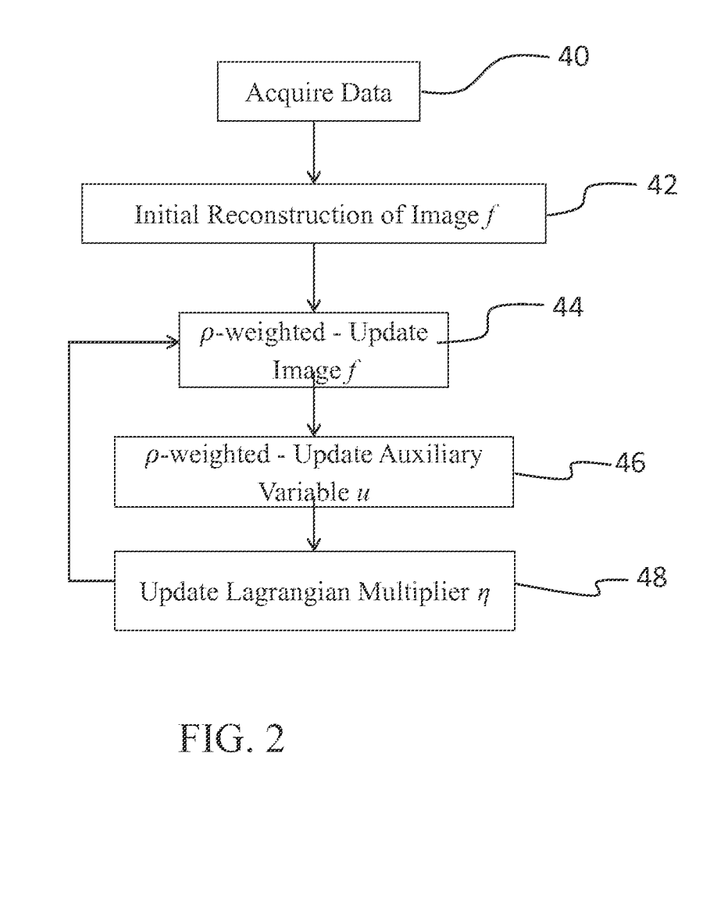
FIG. 2 is a flow diagram of a preferred embodiment iterative computed tomography method of the invention.

The Alternating Direction Method of Multipliers (ADMM) is a technique that can be interpreted as a particular variant of ALM, involving alternating minimization, which is used to make finding the solution more tractable. FIG. 2 shows a preferred embodiment, with the weighting ρ applied to the image discrepancy term (norm tem) in Equation (5), that is, with the ρ-weighted AL in (8). Initial steps involve data acquisition 40 and then the initial reconstruction 42 of the image f. The initial reconstruction can be performed, for example, by a conventional FBP method. Each iteration of the preferred embodiment ADMM algorithm with the ρ-weighted AL involves three steps: (i) update the image 44 by minimizing the ρ-weighted AL $L_\rho$ with respect to f, to a desired degree of accuracy, i.e., perform the minimization in Equation (9) to a desired degree of accuracy, e.g, using a nonlinear iterative conjugate gradient algorithm, while keeping variables u and η fixed at their values at the end of the previous iteration; (ii) update the auxiliary sinogram variable u 46 by minimizing the ρ-weighted AL $L_\rho$ with respect to the auxiliary variable u to a desired degree of accuracy, which, in the case of the PWLS choice for h involves performing the minimization in Equation (10) to a desired degree of accuracy, while keeping f and η fixed; and (iii) gradient update 48 step of the Lagrangian Multiplier variable η while keeping f and u fixed, per Equation (11). This sequence of steps is repeated, until an appropriate convergence (completion) criterion is met. In variations of the FIG. 2 embodiment, the order of the update steps 44, 46, and 48 is modified, and one or more of the updates is performed more than once per iteration. Equations (9)-(11) respectively illustrate the updates of steps 44, 46 and 48, in the case of the PWLS choice for h:

$$f^{n+1} = \underset{f}{\operatorname{argmin}}\, \Phi(f) + \frac{\mu}{2}\|u^n - Rf - \eta^n\|_\rho^2 \quad (9)$$

$$u^{n+1} = \underset{u}{\operatorname{argmin}}\, \frac{1}{2}\|g - u\|_W^2 + \frac{\mu}{2}\|u - Rf^{n+1} - \eta^n\|_\rho^2 \quad (10)$$

$$\eta^{n+1} = \eta^n - (u^{n+1} - Rf^{n+1}) \quad (11)$$

Here, the second term in the cost functions of (9) and (10) is called the image discrepancy term, and the first term in the cost function in (10) is called the sinogram discrepancy term.

The preferred updating with p weighting is labelled "ADMM- ρ". The most challenging step from a computational standpoint is the image update (9) which itself must usually be solved by an iterative method. We call these iterations "inner iterations", and refer to the iterations (for increasing n) over the steps in (9)-(11) as "outer iterations". Through the choice of a ρ weighting, the optimization problem has been implicitly preconditioned. For example, approximating a solution to (9) using a conjugate-gradients (CG) method involves calculating the gradient of the cost function in (9) with respect to f, yielding $$\nabla_f \Phi(f) + \mu R^T \rho (Rf - u^n + \eta^n) \quad (12)$$

which contains the term $R^T \rho R$, which as described before, is a well-conditioned matrix (or operator), approximating an identity operation. Because the convergence rate of CG is affected by the conditioning (more specifically, the clustering of eigenvalues) of the Hessian of the cost function, the convergence of the inner iterations for minimization of (9) will be accelerated by the $\rho$ weighting, resulting in a speedup of the entire process.

Other minimization strategies can be employed in minimizing (9). The ordered subsets (OS) method approximates the gradient calculation of (12) by using only a subset of views, the subsets indexed by in m=1, ..., M, $$\nabla_f \Phi(f) + \mu M R_m^T \rho (R_m f - u_m^n + \eta_m^n) \quad (13)$$

Each of the M subsets contains $$\frac{1}{M}$$

of the original projection angles. The subscript m in (13) is understood to represent the appropriate subset of views in the corresponding variable/operator. Different subsets are used in successive iterations, cycling through them in some desired order. Owing to the dominance of the operator R versus $\Phi$ computationally, the calculations in (13) are approximately M times faster than using the full sinogram data in (12).

The introduction of $\rho$ weighting increases somewhat the complexity of the minimization problem in (10), whose solution has the form $$u^{n+1} = (W + \mu\rho)^{-1}(\mu\rho(Rf^{n+1} + \eta^n) - Wg) \quad (14)$$

The operation $(W+\mu\rho)$ is difficult to invert directly, and similar to (9), an iterative process with a few "inner iterations" is also required, using the gradient with respect to u of the cost function in (10), which is given by $$Wu + \mu\rho(u - Rf^{n+1} - \eta^n) - Wg \quad (15)$$

However, unlike finding the solution of (9), the only operators that need to be applied in the iterative solver used to compute the update in (14) are the diagonal W and the $\rho$ weightings, which are significantly cheaper computationally than the projector R, or backprojector $R^T$, especially if low order projection-domain filter approximations to $\rho$ are used. Finallly, the step in (11) is a simple update and requires negligible computation compared to the other steps.

Alternatively, an additional variable split s=u can be introduced to detangle the application of the W and $\rho$ weightings, allowing for closed-form updates of the auxiliary variables. The $\rho$-weighted AL formulation in this case is $$L_\rho(f, u, s, \eta_u, \eta_s) = \quad (16)$$
$$h(s, g) + \Phi(f) + \frac{\mu_1}{2}\|u - Rf - \eta_u\|_\rho^2 + \frac{\mu_2}{2}\|s - u - \eta_s\|_2^2$$

Variable s is another singoram-domain auxiliary variable, which represents an approximation to the auxiliary sinogram variable u, and which is distinct from all three quantities g, u, and Rf. The $\rho$-weighted AL with the indicated additional variable split in (16) is useful more generally when h(s, g) is a relatively complicated function of s, for example when h(s, g) comprises a statistical model for g such as a negative log likelihood for a Poisson measurement model in SPECT or PET.

Again, applying the ALM algorithm to the $\rho$-weighted augmented Lagrangian in (16), the updates for the different variables can be performed one at a time, in sequence. For the ADMM applied to this AL, the update sequence for one iteration consists of three minimization steps, with respect to the variables f, u, and s, respectively, and two updates for the Lagrangian variables $\eta_u, \eta_s$.

$$f^{n+1} = \operatorname*{argmin}_f \Phi(f) + \frac{\mu_1}{2}\|u^n - Rf - \eta_u^n\|_\rho^2 \quad (17)$$

$$u^{n+1} = \operatorname*{argmin}_u \frac{\mu_1}{2}\|u - Rf^{n+1} - \eta_u^n\|_\rho^2 + \frac{\mu_2}{2}\|s^n - u - \eta_s^n\|_2^2 \quad (18)$$

$$s^{n+1} = \operatorname*{argmin}_s h(s, g) + \frac{\mu_2}{2}\|s - u^{n+1} - \eta_s^n\|_2^2 \quad (19)$$

$$\eta_u^{n+1} = \eta_u^n - (u^{n+1} - Rf^{n+1}) \quad (20)$$

$$\eta_s^{n+1} = \eta_s^n - (s^{n+1} - u^{n+1}) \quad (21)$$

The update for u involves inverting $(\mu_2 I + \mu_1 \rho)$, which is a shift invariant filter and can be efficiently inverted with a pair of FFT applications, or the inverse filter can be approximated by a low order digital filter. The update for s requires, in the PWLS case, inverting $(W+\mu_2 I)$, which is diagonal and has inverse consisting of the inverse of each element along the diagonal. Finally, the two update steps of the Lagrangian variables are each similar to (11) and are similarly simple and require negligible computation compared to the other steps.

A similar additional variable split z=f, using an axillary image variable z that is distinct from f, can be performed in the image domain to detangle the application of the R operator and the regularization calculations $\Phi$, resulting in $$L_\rho(f, u, z, \eta_u, \eta_z) = \quad (22)$$
$$h(u, g) + \Phi(z) + \frac{\mu_1}{2}\|u - Rf - \eta_u\|_\rho^2 + \frac{\mu_2}{2}\|z - f - \eta_z\|_2^2$$

Applying the ALM algorithm to the $\rho$-weighted augmented Lagrangian in (22) yields simpler updates than the original algorithm.

$$f^{n+1} = \underset{f}{\operatorname{argmin}} \frac{\mu_1}{2} \|u^n - Rf - \eta_u^n\|_\rho^2 + \frac{\mu_2}{2} \|z^n - f - \eta_z^n\|_2^2 \quad (23)$$

$$u^{n+1} = \underset{u}{\operatorname{argmin}} h(u, g) + \frac{\mu_1}{2} \|u - Rf^{n+1} - \eta_u^n\|_\rho^2 \quad (24)$$

$$z^{n+1} = \underset{z}{\operatorname{argmin}} \Phi(z) + \frac{\mu_2}{2} \|z - f^{n+1} - \eta_z^n\|_2^2 \quad (25)$$

$$\eta_u^{n+1} = \eta_u^n - (u^{n+1} - Rf^{n+1}) \quad (26)$$

$$\eta_z^{n+1} = \eta_z^n - (z^{n+1} - f^{n+1}) \quad (27)$$

The update for variable f involves a quadratic regularization term instead of the typically non-quadratic $\Phi$ function. The update for variable z does involve $\Phi$, but does not require the R operator at all, leading to a denoising-like update step, which can be solved efficiently. These additional splits in Equations (16) and (22) can be combined, although they are described separately here for clarity.

The stopping criteria for the iterative method can be modified to use the new variables. For example, the sinogram variable u can be compared to the actual measurements g, or to calculated measurements Rf. Or in the case of using the additional auxiliary sinogram variable s as in (16), it can be compared to g, or u can be compared to Rf. The comparison between variables might involve using a desired function of the variables, such as the function h, or a norm or weighted norm. Additionally, the amount of change in any of these variables in a given iteration can be calculated and compared to a threshold. For example, the values of the sinogram discrepancy term and the image discrepancy term may be compared, or one or both terms may be monitored for sufficiently small change from one iteration to another.

The ADMM algorithm is not the only method by which the AL can be minimized. One such alternative is the alternating minimization algorithm (AMA). AMA minimizes the AL through a sequence of simpler update steps. AMA applied to the $\rho$-weighted AL in (8) yields the AMA-$\rho$ procedure $$f^{n+1} = \underset{f}{\operatorname{argmin}} \Phi(f) + \mu \langle \eta^n, Rf \rangle_\rho = \underset{f}{\operatorname{argmin}} \Phi(f) + \mu \langle R^T \rho \eta^n, f \rangle_2 \quad (28)$$

$$u^{n+1} = \underset{u}{\operatorname{argmin}} \frac{1}{2} \|g - u\|_W^2 - \mu \langle \eta^n, u \rangle_\rho + \frac{\mu}{2} \|u - Rf^{n+1}\|_\rho^2 \quad (29)$$

$$\eta^{n+1} = \eta^n - (u^{n+1} - Rf^{n+1}) \quad (30)$$

Here the notation $(a, b)_\rho = a^T \rho b$ denotes the $\rho$-weighted inner product, whereas $(a, b)_2 = a^T b$ denotes the regular (Euclidean) inner product. In (28), we refer to the inner product term as an image discrepancy term, whereas in (29) the image discrepancy term is the third term. This sequence of steps has a simpler form in (28) for the update in the image variable f than in (9): due to the non-quadratic regularizer $\Phi$, the respective updates will require an iterative strategy, but here the backprojector $R^T$ need only be applied once during the minimization with respect to f (because $\eta^n$ remains fixed) whereas in (9) both R and $R^T$ are applied in every iteration in minimizing f. Updates to u and $\eta$ remain comparable to the ADMM algorithm.

Preferred Variations with the Auxiliary Variable Iteration Methods and the $\rho$-weighted AL Linearized ADMM-$\rho$ Embodiment The so-called Linearized ADMM framework (also known as the split inexact Uzawa method) can also benefit from the weighting with $\rho$. A preferred linearized ADMM (L-ADMM) approach modifies the image update step in (9) by adding an additional penalty (or so-called inertia) term. In the typical formulation of L-ADMM (without the $\rho$ weighting), the image update is $$f^{n+1} = \underset{f}{\operatorname{argmin}} \Phi(f) + \frac{\mu}{2} \|u^n - Rf - \eta^n\|_2^2 + \frac{1}{2} \|f - f^n\|_Q^2 \quad (31)$$

where $Q$ must be positive semi-definite, or positive definite. The choice of Q can make finding the solution to (31) much easier. In particular, the main computational burden in minimizing in (31) is the application of the operator R and its adjoint $R^T$. The operator Q is chosen as $$Q = \frac{1}{\delta} I - \mu R^T R \quad (32)$$

The coefficient $\delta$ is must satisfy $\delta \leq 1/\mu \|R^T R\|$ so that Q will be at least positive semi-definite. Here the norm applied to the operator is the induced operator norm equal to the largest singular value in the case of a matrix. The minimization problem of (31) then becomes solving $$f^{n+1} = \underset{f}{\operatorname{argmin}} \Phi(f) + \frac{1}{2\delta} \|f - f^n - \mu \delta R^T (u^n - Rf^n - \eta^n)\|_2^2 \quad (33)$$

A significant improvement is that the operators R and $R^T$ act only on the previous values of each variable and thus only need to be applied once each during the entire minimization in (33) to determine $f^{n+1}$. In contrast, solving (9) via gradient methods requires application of each operator during each inner iteration of the minimization algorithm for solving (9). A potential limitation of L-ADMM is that typically the entire algorithm requires many more outer iterations for convergence. The objective when using L-ADMM is that the increased number of outer ADMM iterations is offset by the improved speed of each outer iteration, in particular solving the image minimization via (33). The convergence of L-ADMM is improved by picking $\delta$ as large as possible, subject to the constraint with respect to the operator R mentioned previously.

Combining L-ADMM with the ρ weighting yields an algorithm with similar structure but significantly improved performance. The choice of operator Q becomes $$Q = \frac{1}{\delta}I - \mu R^T \rho R \qquad (34)$$

The minimization problem of (31) is similarly modified by the inclusion of the ρ weighting in both the second term and in Q, yielding the image update equation as a solution to the minimization problem $$f^{n+1} = \underset{f}{\operatorname{argmin}} \Phi(f) + \frac{1}{2\delta}\|f - f^n - \mu\delta R^T \rho(u^n - Rf^n - \eta^n)\|_2^2 \qquad (35)$$

This improvement concerns the choice of the parameter δ, which now must satisfy $\delta \leq 1/(\mu\|R^T\rho R\|)$. The inclusion of the ρ weighting allows for a larger δ, because $\|R^T\rho R\| \ll \|R^T R\|$. In this variation the image f is updated (step 44 in FIG. 2) by solving Equation (35) to a desired degree of accuracy, e.g, using a nonlinear iterative conjugate gradient algorithm. The update steps for u and η are the same as in Equations (10) and (11), respectively. This modified L-ADMM algorithm has the benefits of reducing the computational effort of the image update step in (9) by replacing it with the update (35) while retaining convergence rates in terms of number of outer iterations comparable to the original ADMM formulation.

Extended Weighting Embodiment

In this variation, the ρ weighting operator is augmented with operator F to form aggregate weighting operator $\Gamma = E^T \rho E$. The operator E is applied on both sides of ρ to maintain symmetry of the operator. The extended weighting operator E can be constructed to make the composite operator $R^T E^T \rho ER$ become closer to an identity operation, i.e. improve the implicit preconditioning nature of the weighting.

For example, E can be a rebinning operation, converting from fan-beam to parallel-beam data. The use of the ρ operator for parallel beam geometries makes $R^T\rho$ a more exact analytical inverse of R than when applied to fan-beam geometries. Similarly in 3D, the E operator can rebin from true cone-beam data to cone-parallel data (parallel in-plane, but divergent beam along the axial direction). Applying the ρ operator on this geometry is equivalent to filtering along slanted lines in the original cone-beam domain, which has been shown to be advantageous in FBP reconstructions. Alternatively, E could simply rotate the projection data on the detector panel itself to implement filtering along slanted lines. The adjoint operation $E^T$ rotates the projection data back to its original orientation. The operator E can also be adopted when using the square root of the ramp filter $$\rho^{\frac{1}{2}}$$

or approximation to a square root of the ramp filter, e.g., in the form $$\rho^{\frac{1}{2}} E.$$

In general, the most effective choice of E, in terms of the approximation of the identity by the composite operator $R^T E^T \rho ER$, would be to make the composite operator $R^T E^T \rho E$ approximate the inverse of R. To the extent that an FBP reconstruction algorithm provides a good approximation to the inverse of R, a good choice for E would result in $R^T E^T \rho E$ behaving like the FBP reconstruction operator.

Alternatively, the weighting operator Γ can be chosen to correspond to filtering along slanted lines or curves in the original cone-beam projection domain (that is, jointly in the variables t, δ, r or a subset thereof, similar to the filtering used in reconstruction procedures for divergent beam CT geometries (e.g. helical coneheam).

The update equations analogous to (9) and (10) replace the ρ weighting by the extended weighting operator $\Gamma = E^T \rho E$. A similar change applies to Equations (12)-(14). As before, the corresponding operation (W+μΓ) is hard to invert directly, and similar to the case of ρ weighting, the minimization with respect to u of the cost function corresponding to the one in (10) is performed by an iterative process with a few "inner iterations" using the gradient with respect to u, which takes the form in (14), with ρ replaced by $\Gamma = E^T \rho E$. The same comments about applying W and Γ at low computational cost apply, except that the application of $\Gamma = E^T \rho E$ will now involve rebirming as well.

As before, the need for an iterative algorithm to compute the update of u can be overcome by introducing another variable split. While the split u=s used before can work in this situation as well, the resulting update for u involves inverting $(\mu_2 I + \mu_1 \Gamma) = \mu_2 I + \mu_1 E^T \rho E$, which is no longer a simple shift invariant filter. Instead, using the split u=Es retains the linear shift invariant filtering form for the u update, and the update for s involves instead inversion of $W + \mu_2 E^T E$. For most rehinning operators E, the operator $E^T E$ will be very well conditioned, and often structured, facilitating inversion or iterative solution.

$$f^{n+1} = \underset{f}{\operatorname{argmin}} \Phi(f) + \frac{\mu_1}{2}\|u^n - E(Rf + \eta_s^n)\|_\rho^2 \qquad (36)$$

$$s^{n+1} = \underset{s}{\operatorname{argmin}} h(s, g) + \frac{\mu_2}{2}\|u^n - Es - \eta_u^n\|_2^2 \qquad (37)$$

$$u^{n+1} = \underset{u}{\operatorname{argmin}} \frac{\mu_1}{2}\|u - E(Rf^{n+1} + \eta_s^n)\|_\rho^2 + \frac{\mu_2}{2}\|u - Es^{n+1} - \eta_u^n\|_2^2 \qquad (38)$$

$$\eta_u^{n+1} = \eta_u^n - (u^{n+1} - Es^{n+1}) \qquad (39)$$

$$\eta_s^{n+1} = \eta_s^n - (s^{n+1} - Rf^{n+1}) \qquad (40)$$

The extended weighting can be combined with the L-ADMM similarly to the way the ρ weighting was combined with the L-ADMM, obtaining the benefit of both features.

Regularizer-Aware Weighting Embodiment

Another variation on the previous choices of weighting operator $\Gamma$, is directed explicitly to improve the conditioning of the Hessian with respect to f $\nabla_f^2 L_\Gamma(u, f, \eta) = R^T\Gamma R + \nabla_f^2 \Phi$ (f) of the $\Gamma$-weighted AL. Typically, with quadratic regularization, $\Phi(f) = \|f\|_G^2$, where G is a weighting operator with a high-pass filter characteristics. This is typically true to a good approximation, even with edge-preserving, non-quadratic regularization, for small values of the image gradient. It follows, that to make the Hessian $\nabla_f^2 L_\Gamma(u, f, \eta)$ well-conditioned, or approximate the identity, the weighting $\Gamma$ can be chosen so that $R^T\Gamma R$ has frequency response complementary to that of G. This can be achieved by replacing the RamLak ramp filter $\rho$ in $E^T\rho E$ by an appropriately apodized (frequency-weighted) ramp filter, with similar modifications when using the square root filter.

Filtering in the Image Domain Embodiment

Artisans will appreciate that the composite operator $R^T\Gamma R$ is an operation that produces an output image from an input image. Hence, this operation can be performed entirely in the image domain. This can lead to savings, if the operation can be performed at lower cost than a projection R or backprojection $R^T$. Now, with the weighting $\Gamma$ chosen to one of the forms described in this invention, so that $R^T\Gamma R$ is well-conditioned or an approximate identity, $R^T\Gamma R$ can be approximated by a low-order and inexpensive digital filtering operation, in the image domain. This will further reduce the cost of the iterative algorithm.

Introduction of $\rho$ through Image Domain Split (left-right) Preconditioner Embodiment In another preferred variation, instead of incorporating the $\rho$ operator in the sinogram domain, it can instead be introduced into the formulation using an image domain representation. Consider the minimization with respect to f of the augmented Lagrangian without the $\rho$ weighting in (5). It involves the solution of the zero gradient condition expressed by the following equation $$\nabla_f \Phi(f) + \mu R^T Rf + \mu R^T(\eta - u) = 0 \qquad (41)$$

This equation for f is typically ill-conditioned because of the ill-conditioning of the Hessian $R^T R$ of the image discrepancy term with respect to f. Denote the image domain representation or approximate representation of the $\rho$ operator as $\hat{\rho}$. For example, when $\rho$ corresponds to the ramp filter with 1-D frequency response $|\omega|$ in the projection domain, the operator $\hat{\rho}$ may be chosen as an image domain filter with frequency response $\sqrt{\omega_1^2 + \omega_2^2}$, where $\omega_1$ and $\omega_2$ denote the frequency variables in the transverse plane. More generally, $\hat{\rho}$ may be chosen as an image domain filter with a high-pass response in the transverse plane. Denote further a square root of tins operator as $$\hat{\zeta} = \hat{\rho}^{\frac{1}{2}}.$$

Then using $\hat{\zeta}$ as a split (combination of left and right) preconditioner in Eq. (41), yields the following preconditioned version of Eq. (41):

$$\hat{\zeta}^T \nabla_f \Phi(f) + \mu \hat{\zeta}^T R^T R \hat{\zeta} x + \mu \hat{\zeta}^T R^T(\eta - u) = 0 \text{ where } f = \hat{\zeta} x \qquad (42)$$

where x is an image-domain auxiliary variable that is related to the image f by the relation $$f = \hat{\zeta} x = \hat{\rho}^{\frac{1}{2}} x.$$

That is, appocanon of the image-domain filer $\hat{\zeta}$ to x produces f. We refer to x as a pre-image. Next, using the identity that holds for a linear operator A: $\nabla_x \Phi(Ax) = A^T \nabla_f \Phi$ (f) whenever f=Ax, Eq. (42) reduces to $$\nabla_x \Phi(\hat{\zeta} x) + \mu \hat{\zeta}^T R^T R \hat{\zeta} x + \mu \hat{\zeta}^T R^T(\eta - u) = 0 \text{ where } f = \hat{\zeta} x \qquad (43)$$

To obtain this preconditioned form of the gradient with respect to x, the AL in Eq. (5) is modified to the following form $$L_\rho(x, u, \eta) = h(u, g) + \Phi(\hat{\zeta} x) + \frac{\mu}{2}\|u - R\hat{\zeta} x - \eta\|_2^2 \text{ where } f = \hat{\zeta} x \qquad (44)$$

Eq. (43) is made to be well-conditioned for solving for the variable x by choosing the image domain filter $\hat{\zeta}$ so that $\hat{\zeta}^T R^T R \hat{\zeta}$ is well-conditioned (e.g., approximates or is proportional to the identity operator), for example by using the square root of the image domain ramp filter as described above, or its approximation using an FIR or an IIR image domain filter, or using the FFT. In the case of an IIR or FIR filter, it may be advantageous to use in the definition $$\hat{\zeta} = \hat{\rho}^{\frac{1}{2}}$$

a square root operator that is not necessarily Hermitian symmetric (or self adjoint); it only needs to satisfy the equation $$(\hat{\rho}^{\frac{1}{2}})^T (\hat{\rho}^{\frac{1}{2}}) = \hat{\rho}.$$

This allows the phase of the frequency response of the filter $$\hat{\rho}^{\frac{1}{2}}$$

to be freely chosen, which may enable a computationally cheaper implementation than in the case of a Hermitian symmetric operator with zero phase frequency response.

An alternative favorable choice for $\hat{\zeta}$ is one that makes the Hessian with respect to x of the AL $L_\rho(x, u, \eta)$, which is given by $$\nabla_x^2 \Phi(\hat{\zeta} x) + \mu \hat{\zeta}^T R^T R \hat{\zeta} \qquad (45)$$

well-conditioned (e.g., approximately equal or proportional to the identity operator).

Because the relation in Eq. (44) between the variables f and x does not appear in the expression for $L_\rho(x, u, \eta)$, the block-coordinate optimization of $L_\rho(x, u, \eta)$ with respect to the variables x, u and $\eta$ can proceed without reference to the image variable f. The image f can be computed only at the end of the iterations, when the completion criterion has been satisfied, or more frequently if desired, e.g., for monitoring the iterations.

The steps corresponding to the ADMM algorithm in this case, i.e. the block-coordinate optimization of $L_\rho(x, u, \eta)$, are analogous to those in Eq. (9)-(11), and in the PWLS case that the sinogram discrepancy term has the form of a weighted two-norm are given by $$x^{n+1} = \operatorname*{argmin}_{x} \Phi(\hat{\rho}^{\frac{1}{2}}x) + \frac{\mu}{2}\left\|u^n - R\hat{\rho}^{\frac{1}{2}}x - \eta^n\right\|_2^2 \quad (46)$$

$$u^{n+1} = \operatorname*{argmin}_{u} \frac{1}{2}\|g - u\|_W^2 + \frac{\mu}{2}\left\|u - R\hat{\rho}^{\frac{1}{2}}x^{n+1} - \eta^n\right\|_\rho^2 \quad (47)$$

$$\eta^{n+1} = \eta^n - \left(u^{n+1} - R\hat{\rho}^{\frac{1}{2}}x^{n+1}\right) \quad (48)$$

In this embodiment the preconditioning operator $$\hat{\rho}^{\frac{1}{2}}$$

advantageously is not directly applied to the auxiliary sinogram variable u, which makes the update steps for u simpler having the closed-form solution, $$u^{n+1} = (W + \mu I)^{-1}\left(\mu\left(R\hat{\rho}^{\frac{1}{2}}x^{n+1} + \eta^n\right) - Wg\right) \quad (49)$$

which only requires multiplication of previously calculated quantities by a diagonal matrix.

The only numerically difficult step is the x image variable update, which will have a similar level of complexity to the f updates of the sinogram-domain ρ operator, e.g. Eq. (9), and can be similarly performed to desired accuracy using an iterative minimization algorithm such as nonlinear conjugate gradients.

Introduction of ρ through image Domain Variable Splitting Embodiment

This is another embodiment with ρ applied in the image domain. The same notation and meaning for $\hat{\rho}$ and $$\hat{\rho}^{\frac{1}{2}}$$

as above is used. This embodiment introduces into Eq. (4) an additional auxiliary image domain variable x with corresponding image domain constraint relating the new image variable x and the original image variable f with the $$\hat{\rho}^{\frac{1}{2}}$$

operator. The resulting equation is $$f_{opt} = \operatorname*{argmin}_{f} h(u, g) + \Phi\left(\hat{\rho}^{\frac{1}{2}}x\right) \quad (50)$$

such that $u = Rf, f = \hat{\rho}^{\frac{1}{2}}x$

Following from the non-ρ weighted case in (5), the extended ρ-weighted Augmented Lagrangian for this is written $$L_\rho(f, x, u, \eta_1, \eta_2) = \quad (51)$$
$$h(u, g) + \Phi\left(\hat{\rho}^{\frac{1}{2}}x\right) + \frac{\mu_1}{2}\left\|u - R\hat{\rho}^{\frac{1}{2}}x - \eta_1\right\|_2^2 + \frac{\mu_2}{2}\left\|f - \hat{\rho}^{\frac{1}{2}}x - \eta_2\right\|_2^2$$

Focusing specifically on the corresponding ADMM update equations for f and $\eta_2$ for this Augmented Lagrangian, we have $$f^{n+1} = \operatorname*{argmin}_{f}\left\|f - \hat{\rho}^{\frac{1}{2}}x^{n+1} - \eta_2^n\right\|_2^2 = \hat{\rho}^{\frac{1}{2}}x^{n+1} + \eta_2^n \quad (52)$$

$$\eta_2^{n+1} = \eta_2^n - \left(f^{n+1} - \hat{\rho}^{\frac{1}{2}}x^{n+1}\right) \quad (53)$$

With the initialization $\eta_2^0 = 0$, these recurrence relations resolve to $$f^{n+1} = \hat{\rho}^{\frac{1}{2}}x^{n+1}, \eta_2^n = 0,$$

allowing the $\eta_2$ term and update equation to be dropped all together.

The modified set of ADMM update equations for all variables are then $$x^{n+1} = \operatorname*{argmin}_{x} \Phi\left(\hat{\rho}^{\frac{1}{2}}x\right) + \frac{\mu_1}{2}\left\|u^n - R\hat{\rho}^{\frac{1}{2}}x - \eta_1^n\right\|_2^2 + \frac{\mu_2}{2}\left\|f^n - R\hat{\rho}^{\frac{1}{2}}x\right\|_2^2 \quad (54)$$

$$u^{n+1} = \operatorname*{argmin}_{u} \frac{1}{2}\|g - u\|_W^2 + \frac{\mu_1}{2}\left\|u - R\hat{\rho}^{\frac{1}{2}}x^{n+1} - \eta_1^n\right\|_2^2 \quad (55)$$

$$\eta_1^{n+1} = \eta_1^n - \left(u^{n+1} - R\hat{\rho}^{\frac{1}{2}}x^{n+1}\right) \quad (56)$$

$$f^{n+1} = \hat{\rho}^{\frac{1}{2}}x^{n+1} \quad (57)$$

This embodiment shares the benefits of the above image domain embodiment defined by Equations (44) and (46)-(49), particularly the preconditioning operator is not directly applied to the auxiliary sinogram variable u, which makes the update steps for u simpler and they may have closed-form solutions. The update step for f also has a trivial closed-form in this formulation. The only numerically difficult step is the x image variable update, which will have a similar level of complexity to the f updates of the sinogram-domain ρ operator, e.g. (9), and can be similarly performed to desired accuracy using an iterative minimization algorithm such as nonlinear conjugate gradients. However, in this embodiment and Equations (51)-(57) above the quantities f and $$\rho^{\frac{1}{2}}x$$

are distinct, which can provide additional freedom and improve the speed of convergence.

Additional Variations

The particular examples of using the different variants of weighting operators Γ of this invention with the alternating minimization of the ρ-modified AL in the ADMM-ρ and L-ADMM-ρ algorithms are not meant to be exhaustive. The different variants of weightings and iterative schemes can be combined in various ways. The same weighting operators can be used to provide similar advantages in other alternating minimization schemes known in the art, for example versions studied of Gauss-Seidel and of the so-called diagonal-quadratic approximation method [J. Eckstein, "Augmented Lagrangian and Alternating Direction Methods for Convex Optimization: A Tutorial and Some Illustrative Computational Results," RUTCOR Research Report RRR 32-2012, December 2012], or DQA, or related methods such as Gradient projection for sparse reconstruction (GPSR) [M. T. Figueiredo, R. D. Nowak, and S. J. Wright, Gradient projection for sparse reconstruction: Application to compressed sensing and other inverse problems, 2007], Proximal Forward-backward splitting methods (PFBS) [P. L. Combettes and V. R. Wajs, Signal recovery by proximal forward-backward splitting, 2005], and Uzawa-type iterations, or as another set of examples, versions with Nesterov-type or Barzilai-Borwein type acceleration of the inner and/or the outer iterations in versions of the ALM or ADMM or L-ADMM, such as NESTA, FISTA, etc.

Artisans will also appreciate that the description and embodiments of different variations of this invention can be modified and manipulated to other, mathematically equivalent forms, in which not all features previously described would be apparent. For example, auxiliary sinogram variables u and η in Eqns. (8)-(12) could be represented together by a single vector, say v, by stacking the vectors u and η as $v=[u^T, \eta^T]^T$. Eqns. (8)-(12) could then be rewritten in terms of the single auxiliary sinogram variable v, with a corresponding change in any computer code or system executing the instructions to perform the operations indicated by these equations, obscuring the actual presence of more than one auxiliary variable. The distinct update steps for u and η in FIG. 2 may then also be replaced by a more elaborate single update of variable v.

Simulation Result

A brief example demonstrates the efficacy of the present approach for the PWLS formulation of the cost function. The projection data used is simulated from a thorax phantom, scanned in a 2D fan beam geometry with curved detector panel. The projection data has 983 detectors and 1024 views over a full circular rotation. Poisson noise was added to the simulated data, such that the standard deviation of the noise in the FBP reconstruction was around 20 HU. The baseline iterative algorithm solves (2) using the method of conjugate gradients (CG). The majority of the computation will involve the application of R or $R^T$, so the computational cost of the algorithm will be measured in terms of the number of such operator applications. For example, in CG, each iteration calculates the gradient of (2), which involves application of both R and $R^T$, yielding 2 applications per iteration.

Figure 3:
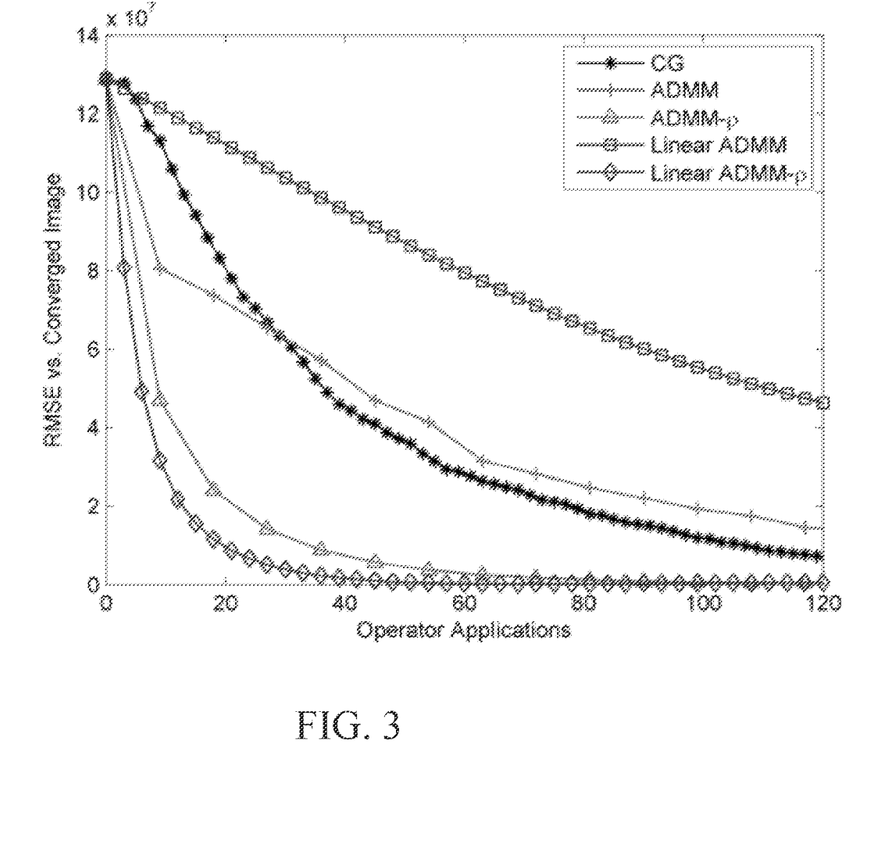
FIG. 3 is a data plot comparing the convergence rate of preferred embodiments (ADDM-ρ and Linearized ADMM-ρ) computed tomography method to prior methods (CG, ADMM, Linearized ADMM).

We consider the resulting image after 200 CG iterations to be the converged image. For each approach, we calculate the progress of the algorithm as the distance or root-mean-square error (RMSE) from this converged image. FIG. 3 plots this RMSE error versus computational cost to compare the effective convergence rates. For reference, 200 CG iterations would require 400 operator applications. For each method, we tuned the μ parameter for optimal convergence, and for linearized ADMM algorithms set $\delta=0.95 \; (\mu\|R^T R\|)^{-1}$ or $\delta=0.95 \; (\mu\|R^T \rho R\|)^{-1}$, as appropriate.

As FIG. 3 demonstrates, the use of ADMM by itself does not necessarily confer accelerated convergence. Indeed, the convergence of ADMM is qualitatively similar to the CG algorithm for this case. However, incorporation of the ρ weighting operator (ADMM-ρ) provides tremendous improvement: the same reduction in RMSE as achieved by CG in 120 operator applications, is achieved by ADMM-ρ in as few as 45 operator applications, corresponding to an almost 3 fold speedup of ADMM-ρ over CG. Similarly, linearized ADMM makes the image update steps computationally easier at the expense of the convergence rate. The linearized ADMM-ρ, on the other hand, takes advantage of better conditioning to further improve the convergence rate: the same reduction in RMSE as achieved by CG in 120 operator applications, is achieved by linearized ADMM-ρ in just 25 operator applications, corresponding to an almost 5 fold speedup of linearized ADMM-ρ over CG.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims. In the claims, when it is stated that some quantity q is a function of another quantity x, this functional dependence is not exhaustive, that is, quantity q can be also a function of some additional quantities. Thus we say that h(s, g) is a function of s, a function of g, and function of both s and g.

The invention claimed is:

1. An iterative image reconstruction method for use in computed tomography (CT), the method comprising:

deriving or receiving a set of actual measurements from an acquired set of actual CT data;

initially constructing an image f;

calculating a set of measurements Rf based on the image f;

generating one or more auxiliary sinogram variables u, η, s, $η_u$, $η_s$ that are distinct from both the set of actual measurements and the set of calculated projections Rf;

determining whether a completion criterion is satisfied;

if the completion criterion is satisfied, providing the image f as a final image; and if the completion criterion is not satisfied:

updating the image f, wherein the image update has at least one of the following properties: (a) the update is in a descent direction with respect to the image of a cost function that comprises an image discrepancy term, the image discrepancy term being a function of the image f and of at least one of the auxiliary sinogram variables u, η, s, $η_u$, $η_s$; and (b) the update is a function of a vector exactly or approximately proportional to the gradient with respect to the image of the image discrepancy term;

updating a first auxiliary sinogram variable u wherein at least one update of u has at least one of the following properties:

(c) the update is in a descent direction with respect to the first auxiliary sinogram variable u of a cost function that includes an image discrepancy term, the image discrepancy term being a function of the projections Rf and of the auxiliary sinogram variable u;

(d) the update is a function of a vector exactly or approximately proportional to the gradient with respect to u of the image discrepancy term, updating one of first and second auxiliary variables u and s, wherein at least one update of the one of first and second auxiliary variables u and has at least one of the following properties:

(e) the update is in a descent direction with respect to the one of first and second auxiliary variables u and s of a cost function that includes a sinogram discrepancy term, the sinogram discrepancy term being a function of the one of first and second auxiliary variables u and s and of the actual measurements; and (f) the update is a function of a vector exactly or approximately proportional to the gradient with respect to the one of first and second auxiliary variables u and s of the sinogram discrepancy term;

wherein in at least one of the image f update and the first auxiliary sinogram variable u update, the respective image discrepancy term is chosen such that its Hessian with respect to the image is well-conditioned, or the Hessian with respect to the image of the sum of the image discrepancy term and a regularization term is well-conditioned; and repeating the steps of determining, updating the image, and updating the at least one of the first and second auxiliary sinogram variables until the completion criterion is satisfied.

2. The method of claim 1, wherein said determining comprises at least one of applying a converge criterion and comparing the number of iterations executed, to a predetermined threshold.

3. The method of claim 1, wherein the convergence criterion further comprises at least one of:

comparing a measured sinogram derived from the set of actual CT data to at least one of the first and second auxiliary sinogram variables u or s;;

comparing a calculated sinogram derived from the set of calculated measurements to least one of the first and second auxiliary sinogram variables u or s;;

comparing a function of at least one of the first and second auxiliary sinogram variables u or s to a threshold.

4. The method of claim 1, wherein:

said deriving or receiving comprises deriving an actual measured sinogram g that are the set of actual measurements; and said determining comprises one of:

comparing the set of actual measurements g to at least one of the auxiliary sinogram variables u or s;

comparing the set of calculated measurements Rf to at least one of the auxiliary sinogram variables u and s;

comparing a function of at least one of the variables to a threshold;

comparing the number of iterations executed, to a predetermined threshold.

5. The method of claim 1, wherein the image discrepancy term between the auxiliary sinogram variable u and calculated measurements of the image, Rf comprises an operator Γ or ρ that is one of a ramp filter, an approximate ramp filter, a square root of the ramp filter, or an approximation to a square root of the ramp filter.

6. The method of claim 5, wherein the operator Γ or ρ is at least one of an IIR filter, an FIR filter, or is applied using an FFT.

7. The method of claim 5, comprising applying the operator in the image domain.

8. The method of claim 5, wherein the operator Γ or ρ is weighted.

9. The method of claim 1, comprising applying a rebinning operation during said updating of the image or said updating of at least one of the auxiliary variables u or s.

10. The method of claim 1, comprising applying a projection rotation operation during said updating of the image or said updating of at least one of the auxiliary variables.

11. The method of claim 1, wherein said applying the image update comprises applying an ordered subsets (OS) minimization of a cost function using subsets of the calculated measurements.

12. The method of claim 1, comprising alternating said updating the image and said updating at least one of the auxiliary variables to jointly minimize a cost function.

13. The method of claim 12, wherein the minimization process comprises one of ADMM (alternating direction method of multipliers), linearized ADMM, AMA (alternating minimization algorithm), Nesterov Accelerated ADMM, or Barzilai-Borwein Accelerated ADMM.

14. The method of claim 1 wherein said operations applied to the image to perform the updating of the image consist of image-domain operations.

15. The method of claim 1, wherein the sinogram discrepancy term comprises a weighting matrix.

16. The method of claim 15, wherein the image discrepancy term includes an image discrepancy weighting operator chosen such that the Hessian with respect to the image of the image discrepancy term is well-conditioned, and wherein an additional auxiliary sinogram variable is used to decouple application of the weighting matrix from the application of the image discrepancy weighting operator to the auxiliary sinogram variables.

17. The method of claim 1, wherein the sinogram discrepancy term is a function of the auxiliary sinogram variable s that is distinct from other auxiliary sinogram variables u and $\eta_u$ of which the image discrepancy term is a function.

18. The method of claim 12, wherein the cost function comprises:
an auxiliary image variable z distinct from the image f that is being updated;
a non-quadratic regularizer, which is applied only to the new image variable;
a discrepancy term comparing the new image variable to the image f that is being updated,
and the method further comprises determining the calculated measurements Rf based on the image f that is being updated.

19. The method of claim 1, wherein the image discrepancy term contains the first auxiliary sinogram variable u, and the sinogram discrepancy term contains the second auxiliary sinogram variable s distinct from the first auxiliary sinogram variable u, and wherein the method further comprises:
generating an update of the first auxiliary sinogram variable u, wherein the update has at least one of the following properties: (a) the update is in a descent direction with respect to the first auxiliary variable of a cost function that includes the image discrepancy term but not the sinogram discrepancy term; and (b) the update is a function of a vector exactly or approximately proportional to the gradient of the image discrepancy term with respect to the first auxiliary variable;
generating an update of the second auxiliary variable s whereby the update has at least one of the following properties: (c) it is in a descent direction with respect to the second auxiliary variable of a cost function that includes the sinogram discrepancy term but not the image discrepancy term; and (d) it is a function of a vector exactly or approximately proportional to the gradient with respect to the second auxiliary variable of the sinogram discrepancy term.

20. A computer tomography system that performs the method of claim 1, wherein the CT data is acquired by an x-ray CT scanner and remaining method steps are performed by an image reconstructor.

21. In a computer tomography system comprising an image reconstructor, code for iteratively reconstructing a sequence $f^n$ of images by a statistical iterative reconstruction algorithm, wherein a set of actual CT data is obtained and a set of actual projections g is calculated therefrom, and wherein a set $Rf^n$ of calculated projections of the reconstructed image sequence is determined during the statistical iterative image reconstruction, and wherein at least one auxiliary sinogram variable u distinct from (i) the set of actual CT data; from (ii) the set of actual projections; and from (iii) the set of calculated projections is applied to iteratively update during the statistical iterative image reconstruction, and wherein in at least some iterations of the statistical iterative reconstruction algorithm an image update has at least one of the following properties: (a) the image update is in a descent direction of a cost function that includes an image discrepancy term between the at least one auxiliary sinogram variable and the set of calculated projections; and (b) the image update is a function of a vector exactly or approximately proportional to the gradient-with-respect-to- the-image of the image-discrepancy-term; and wherein at least one auxiliary sinogram variable has an update with at least one of the following properties: (c) the update is in a descent direction with respect to the auxiliary sinogram variable of a cost function that includes an image discrepancy term, the image discrepancy term being a function of the calculated projections Rf and of the auxiliary sinogram variable; and (d) the update is a function of a vector exactly or approximately proportional to the gradient with respect to u of the image discrepancy term;
wherein in at least one of the image f update and the auxiliary sinogram variable u update, the respective image discrepancy term is chosen such that its Hessian with respect to the image is well-conditioned, or the Hessian with respect to the image of the sum of the image discrepancy term and a regularization term is well-conditioned;
and terminating the statistical iterative reconstruction upon satisfaction of a completion criterion.

22. In a computer tomography system comprising an image reconstructor, code for iteratively reconstructing a sequence of images $f^n$ by a statistical iterative reconstruction algorithm, the image reconstructor iteratively reconstructing a sequence of images by a statistical iterative reconstruction algorithm, wherein a set of actual measurements g is generated from a set of scan data, and wherein at least one auxiliary image variable x distinct from the reconstructed image is used, and wherein at least one auxiliary sinogram variable u distinct from both the set of actual measurements and from a set of calculated measurements Rf is used, and wherein in at least some iterations of the statistical iterative reconstruction algorithm an update of the auxiliary image variable has at least one of the following properties: (a) the update is in a descent direction of a cost function that comprises an image discrepancy term between an auxiliary sinogram variable and measurements calculated based on the auxiliary image variable, and the image discrepancy term or the auxiliary image variable are chosen such that the Hessian of the image discrepancy term with respect to the auxiliary image variable is well-conditioned; and (b) the update is a function of a vector exactly or approximately proportional to the gradient with respect to the auxiliary image variable of the image discrepancy term;
and terminating the statistical iterative reconstruction upon satisfaction of a completion criterion.

23. The image reconstructor of claim 22, wherein the image discrepancy term between an auxiliary sinogram variable and measurements calculated based on the auxiliary image variable, comprises an operator $\Gamma$ that is applied in the image domain, and is the square root of an image-domain ramp filter, or an approximation thereto.

24. The image reconstructor of claim 22, wherein the at least one auxiliary sinogram variable u and the least one new auxiliary image variable x are updated in an alternating fashion, to jointly minimize a cost function.

25. The image reconstructor of claim 24, wherein the minimization process is ADMM.

26. The image reconstructor of claim 22, wherein in at least some iterations of the statistical iterative reconstruction algorithm an update of the auxiliary image variable has at least one of the following properties:
  (a) the update is in a descent direction of a cost function that comprises an image discrepancy term between the auxiliary image variable and the reconstructed image sequence, the discrepancy term further comprising an operator F that is applied in the image domain, and is the square root of an image-domain ramp filter, or an approximation thereto.

\* \* \* \* \*